US012688931B2

(12) United States Patent
Byard et al.

(10) Patent No.: US 12,688,931 B2
(45) Date of Patent: Jul. 21, 2026

(54) ENHANCED BATCH ANALYSIS AND DEVICE PERFORMANCE DETERMINATION WITH USER INTERFACE

(71) Applicant: Analog Devices International Unlimited Company, County Limerick (IE)

(72) Inventors: Julie Byard, Huntingdon (GB); Anna Zvikhachevskaya, Hertford (GB)

(73) Assignee: ANALOG DEVICES INTERNATIONAL UNLIMITED COMPANY, County Limerick (IE)

( * ) Notice: Subject to any disclaimer, the term of this patent is extended or adjusted under 35 U.S.C. 154(b) by 179 days.

(21) Appl. No.: 18/499,038

(22) Filed: Oct. 31, 2023

(65) Prior Publication Data

US 2025/0140393 A1     May 1, 2025

(51) Int. Cl.
G16H 40/40          (2018.01)

(52) U.S. Cl.
CPC ................................... G16H 40/40 (2018.01)

(58) Field of Classification Search
CPC ...... G16H 40/40; G16H 10/40; A61B 5/1495; G06N 3/08; G06N 20/00; G06N 20/10; G06N 20/20
See application file for complete search history.

(56) References Cited

U.S. PATENT DOCUMENTS 11,402,817 B2 *   8/2022   Kubo ................. G05B 19/4065
2019/0274598 A1   9/2019   Scott et al.

FOREIGN PATENT DOCUMENTS

EP          4120653 A1 *   1/2023   ........... H04L 41/147

OTHER PUBLICATIONS

Lauzier, "Predictive Analytics in Manufacturing: Use Cases and Benefits" MachineMetrics, Manufacturing Analytics retrieved from: https://www.machinemetrics.com/blog/predictive-analytics-in-manufacturing dated Dec. 23, 2020 (Year: 2020).*

(Continued)

*Primary Examiner* — Linh Giang Le
(74) *Attorney, Agent, or Firm* — Knobbe, Martens, Olson & Bear, LLP

(57) ABSTRACT

Systems and methods for glucose device batch analyses. An example method includes obtaining analysis datasets reflecting manufacturing information associated with medical devices included in a device batch, the manufacturing data measuring information associated with individual manufacturing steps, and with the analysis datasets being formatted for input into a machine learning model, and with unique identifying information associated with the medical devices being used to aggregate analysis datasets specific to the medical devices. The analysis datasets are provided to the machine learning model, with the machine learning model being trained to output performance information for individual medical devices indicating whether they are in releasable condition. The machine learning model was trained based on ground truth associated with manufactured devices, and the ground truth was derived based on test information associated with the manufactured devices. An interactive user interface is generated which presents summary information associated with the performance information.

20 Claims, 7 Drawing Sheets

(56) References Cited

OTHER PUBLICATIONS

Lauzier, "Predictive Analytics in Manufacturing: Use Cases and Benefits" MachineMetrics, Manufacturing Analytics retrieved from: https://www.machinemetrics.com/blog/predictive-analytics-in-manufacturing dated Dec. 23, 2020 in 7 pages.

Extended European Search Report for International Application No. 24209301.1 dated Mar. 7, 2025 in 9 pages.

Amini Mohammadhossein et al. "MLCPM: A process monitoring framework for 3D metal printing in industrial scale", Computers & Industrial Engineering, Pergamon, Amsterdam, NL, vol. 124, Jul. 26, 2018 (Jul. 26, 2018), pp. 322-330.

Uhlmann Eckart et al. "Intelligent Pattern Recognition of a SLM Machine Process and Sensor Data", vol. 62, Dec. 31, 2017, pp. 464-469.

* cited by examiner

Example Manufacturing Data

154

| Serial | ChipID | Wafer | LeftSensorY | RightSensorY | SensorX | DAB Comments | LeakRate | FlowRate |
|---|---|---|---|---|---|---|---|---|
| 17-07-06-00011 | 0513 | 129252_12 | -0.002 | -0.001 | -0.012 | | 0.40000001 | 3734 |
| 17-07-06-00025 | 2204 | 129252_09 | 0 | -0.003 | -0.001 | 3x DAB | 0.31999999 | 3500 |
| 17-07-07-00023 | 1407 | 129252_09 | 0.012 | 0.022 | 0.002 | | 0.34 | 3742 |
| 17-07-10-00005 | 1109 | 129252_09 | 0.014 | -0.009 | 0.004 | flag pass - particles on O2 sensor | 0.36000001 | 3680 |
| 17-07-11-00006 | 1119 | 129252_09 | 0.007 | -0.014 | -0.005 | flag pass - particles on O2 sensor | 0.41999999 | 3719 |
| 17-07-11-00033 | 0810 | 129252_09 | 0.017 | 0.009 | -0.002 | | 0.31999999 | 3255 |
| 17-07-11-00043 | 0709 | 129252_09 | 0.023 | 0.027 | -0.001 | | 0.22 | 3606 |
| 17-07-11-00060 | 0509 | 129252_09 | 0.007 | 0.007 | 0.005 | | 0.22 | 3708 |

Training Analysis Datasets for Device

Manufacturing Data 202
- Tolerance Data
- Placement Data
- Temperature Data
- Geometry Analyses Test Data for Analyte A 204A
- Blood Gas Analyzer Values
- Correlated Measurements
- In Specification

. . .

Test Data for Analyte N 204N
- Blood Gas Analyzer Values
- Correlated Measurements
- In Specification

300

302

Obtain analysis datasets for subset of glucose devices included in device batch

304

Provide analysis datasets to machine learning model

306

Obtain output indicating performance associated with subset

308

Generate user interface data associated with output

ENHANCED BATCH ANALYSIS AND DEVICE PERFORMANCE DETERMINATION WITH USER INTERFACE

BACKGROUND

Technical Field

The present disclosure relates to analyzing devices, and more particularly, to determining estimates of performance for glucose devices.

Description of Related Art

Glucose, and other health, devices are complex to manufacture and require a high level of accuracy in all manufacturing steps. Typically, devices are manufactured by adhering to strict manufacturing processes. These processes may include testing of different devices at different manufacturing steps, with the testing informing whether the devices will proceed to a subsequent manufacturing step.

Such testing may limit an extent to which devices are able to be manufactured and used by end-users or by researchers. For example, the testing may consume a substantial amount of time. Additionally, the testing may have unclear outcomes. For example, a test may quantity a particular aspect associated with a manufacturing step (e.g., placement of a portion of the device). In this example, it may be unclear which quantitative value or range of values should lead to a device being rejected.

Figure 1A:
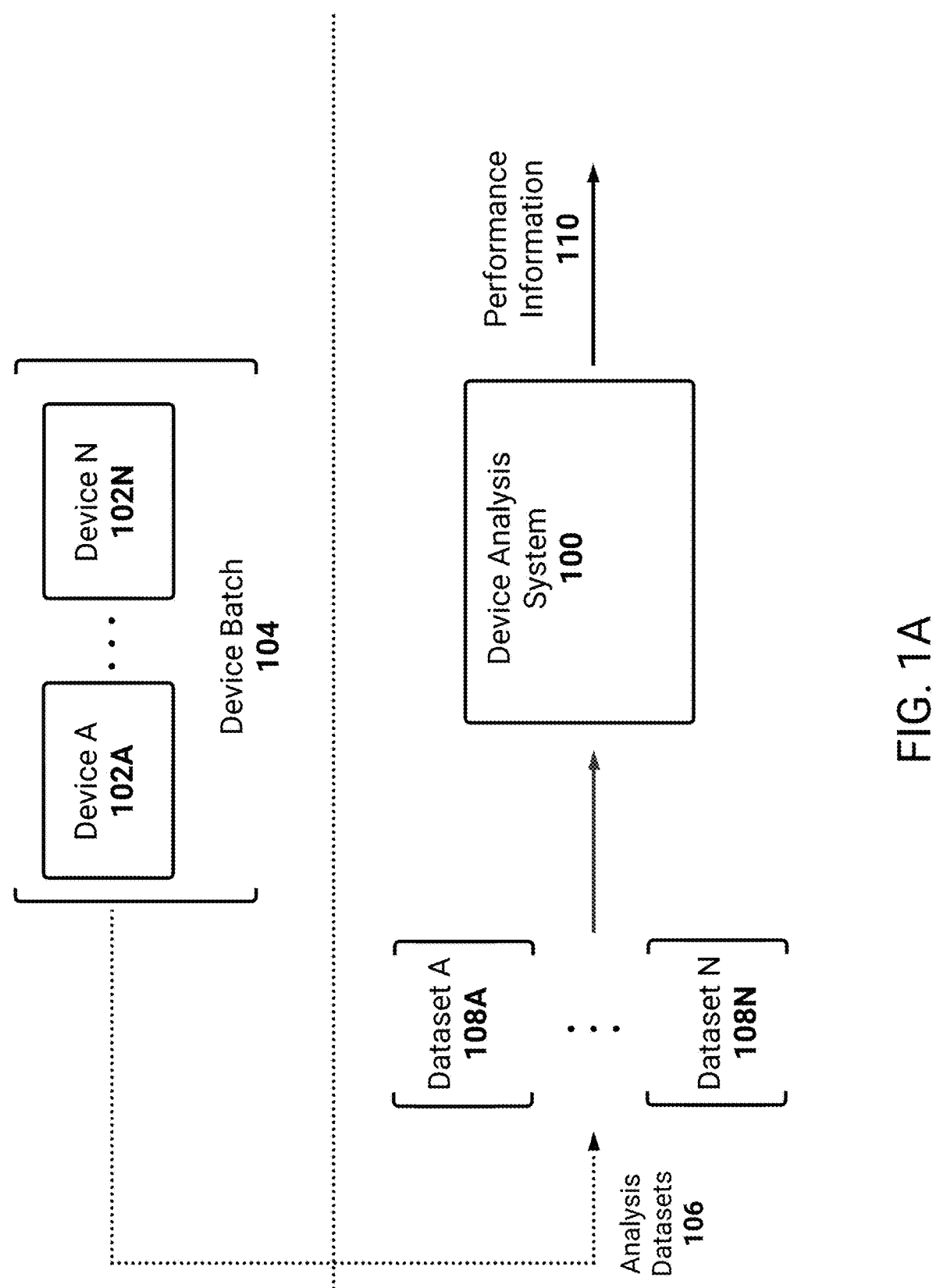
FIG. 1A is a block diagram of an example device analysis system determining performance information associated with a device batch.

Embodiments of the present disclosure and their advantages are best understood by referring to the detailed description that follows. It should be appreciated that like reference numerals are used to identify like elements illustrated in one or more of the figures, wherein showings therein are for purposes of illustrating embodiments of the present disclosure and not for purposes of limiting the same.

DETAILED DESCRIPTION

Introduction

This application describes techniques to analyze performance of devices which are being manufactured or which have been fully manufactured. For example, the devices may be included in a batch of devices. In some embodiments, the devices may be medical devices such as glucose devices. As will be described, a subset of the batch of devices may be analyzed according to the techniques described herein. Based on analyses of this subset, for example using machine learning techniques, performance of the batch may be determined. While a subset is described, in some embodiments information from all devices in a batch may be analyzed.

Performance, in this application, may refer to a score or value indicative of the performance of a device. As an example with respect to a score, the score may indicate a pass or fail which is associated with the device. For this example, a pass score may indicate that the device is in a releasable condition. In some embodiments, there may be a multitude of scores which are associated with different aspects of the device. With respect to a medical device, and as may be appreciated, the device may be designed to detect a number of analytes. Example analytes may include glucose, creatinine, sodium, potassium, phosphate, uric acid, cholesterol, and so on. In these embodiments, there may be individual scores for individual analytes indicating whether the device is able to reliably detect the individual analytes. A pass, in some embodiments, may indicate an accuracy associated with detection greater than a threshold. As an example with respect to a value, performance may indicate a value within a range of values. For example, the range may be between 0 and 1 and the value may be selected within the range. Similar to the above, there may be individual values for individual analytes.

As will be described, the performance information may be output via machine learning techniques. An example machine learning technique may include clustering techniques (e.g., k-means clustering). Another example machine learning technique may include a support vector machine. Another example machine learning technique may include a neural network. Additional example machine learning techniques may be utilized and fall within the disclosure herein. For example, the techniques may include decision trees, logistic regression classifiers, discriminant analysis, and so on.

Using machine learning techniques, a batch of devices may be more reliably characterized as being releasable based on analyzing a subset of the batch. For example, a threshold number of devices included in the batch may be analyzed (e.g., 1 device, 2 devices, 5 devices, 10% of the devices, 15% of the devices, and so on). Due to use of a trained machine learning model, or models, a lesser quantity of devices from a batch may be analyzed to reliably characterize the overall batch. For example, prior techniques relied upon testing a substantial number of devices.

Advantageously, in some embodiments a batch of devices may be characterized based on information only from manufacturing of the devices. As an example, manufacturing information may include how accurately certain components were placed. Manufacturing information may additionally include temperature variability of certain components during manufacturing. This manufacturing information may, in some embodiments, be used to inform whether the batch of devices is expected to be releasable. Additional testing may optionally then be performed based on this automated or semi-automated initial check.

This application therefore improves upon prior technical schemes to ensure performance of important medical devices. Prior techniques required time-intensive testing of large numbers of devices to inform whether batches could be released. These techniques may therefore introduce significant lag into releasing devices. Furthermore, the use of prior techniques via performing final tests of devices may mask which manufacturing stages are prone to error or more significant with respect to causing devices to be un-releasable. In contrast, the techniques described herein may allow for insight into the impact on final performance based on variability within manufacturing stages. As an example, weights in a machine learning model which are associated with manufacturing data may inform their impact on performance. As another example, ablation studies may be used to inform the importance of specific manufacturing data in a neural network.

Thus, this application describes techniques to input aggregated information associated with a batch of devices into a machine learning model. The information may be from disparate sources, with the sources referred to herein as analysis datasets. Example analysis datasets may reflect, in some embodiments, the manufacturing data described above. In some embodiments, manufacturing data may be used in combination with certain test data to determine performance information. For example, testing (e.g., limited testing) may be performed, such as responses to analytes, and so on. Manufacturing data may optionally be automatically obtained from systems which perform, control, or are otherwise associated with, different manufacturing stages. Similarly, testing data may, in some embodiments, be automatically obtained.

For example, and with respect to manufacturing data, a system which is associated with placement of a component may monitor the final placement of the component. In this example, the system may identify a metric associated with a distinction in the placement from a desired placement. The system may optionally obtain image data, or other sensor data, to determine the metric. Thus, the placement information may be obtained and used as input data to characterize performance. As another example, and with respect to testing data, a system may test a multitude of analytes via automated placement of materials on a manufactured device.

The system described herein (e.g., the device analysis system 100) may use the above-described analysis datasets to determine performance information. As will be described, the system may process the analysis datasets to determine information specific to a subset of devices. For example, the system may access metadata or information uniquely identifying a device. In this example, the information may be a serial number associated with the device. The system may then generate summary information based on the analysis datasets. As an example, the system may determine measures of central tendency of disparate information. In this way, lesser information may be provided to the machine learning model described herein. In some embodiments, the summary information may be specific to individual analytes.

The system may then determine output from a machine learning model (e.g., via computing a forward pass through the machine learning model) to obtain performance information. As described above, in some embodiments the performance information may characterize a device as being in a releasable condition. The machine learning model may advantageously be updated based on devices which are released to the public or researchers. For example, members of the public may return devices and these devices may be used as ground truth data.

As will be described, the machine learning model may be trained based on a combination of manufacturing data and testing data. For example, training data may be generated which aggregates manufacturing data and testing data for specific devices. In this example, the testing data may be used to determine ground truth. In some embodiments, the ground truth may reflect a binary value indicating whether the device is accurate to greater than a threshold percentage or value, performs within specification, and so on. The machine learning model may then be trained based on input of manufacturing data and the ground truth. In this way, the machine learning model may learn to map manufacturing data for a device to whether the device is expected to be releasable.

Example Block Diagrams

FIG. 1A illustrates a device batch 104 that includes a multitude of devices A-N 102A-102N. As described herein, the devices may be medical devices such as glucose devices. The devices 102A-102N may more generally measure information relevant to health and be designed to detect a multitude of analytes. The devices 102A-102N may additionally reflect devices which were manufactured and able to be tested. For example, the devices 102A-102N may have undergone a manufacturing process with a multitude of different manufacturing steps.

Each step, or a subset of steps, may generate data which characterizes performance of the devices 102A-102N. Example manufacturing data may include temperature calibration data. For this example, the data may include how precise a temperature a component reaches during manufacturing. The data may also reflect variance in temperature during the manufacturing process. Additional example manufacturing data may include placement data. For this example, the data may describe how well/precise (e.g., a metric) a component (e.g., a chip) is glued or aligned on a printed circuit board (PCB). Additional example manufacturing data may include Anti-Interferent Application data. For this example, the manufacturing data may relate to deposition of a thin layer usable to protect against interferents (e.g., uric acid, paracetamol). Additional example manufacturing data may include environmental data (e.g., humidity data), production data (e.g., pass/fail for each manufacturing stage, uniformity of an enzyme on the device), and so on. Further description regarding manufacturing data is included below with respect to FIG. 2A.

In addition to manufacturing data, testing data associated with the devices 102A-102N may be accessed. The testing data may relate to, for example, a subset of the devices. As an example, a threshold number of threshold percentage of the devices 102A-102N may be tested. Example testing data may include response values (e.g., $H_2O_2$/paracetamol response). Additional example testing data may include blood lab data. For example, the blood lab data may measure disparate functioning aspects of the devices using blood. In this example, the blood lab data may reflect measured responses to different analytes.

As will be described below, with respect to FIG. 2B, the testing data may be processed to generate summary information. For example, an error percentage or value may be determined which reflects a difference between an expected measurement for an analyte and a device's measurement. In this example, the average error percentage or value may be determined across all analytes. Thus, the average error percentage or value may summarize the more detailed information while preserving the device's accuracy with respect to analytes. Summary data may also include a binary value which is indicative of whether a device is in-specification. For example, the system 100 may count a number of instances in which a device performed in-specification and divide it by the total number of readings. In this example, the device may be considered in-specification, and thus have a positive binary value, if the division is greater than a threshold (e.g., 65%, 70%, 75%, and so on). Further description regarding testing data is included below with respect to FIG. 2A.

The above-described information may thus form the analysis datasets 106 of FIG. 1A. The datasets 106 may, in some embodiments, be aggregated or concatenated for each of the devices included in the subset. For example, a vector or row may be generated for each device which includes manufacturing data and testing data. In this example, unique identifying information associated with the device (e.g., serial number) may be used to aggregate or concatenate the data.

The device analysis system 100 may then determine performance information 110 for the device batch 104. In some embodiments, the performance information 110 may reflect a binary value indicating whether a device included in the subset is in a releasable condition. The system 100 may execute a machine learning model, such as a support vector machine to assign the binary value. The system 100 may also execute a neural network (e.g., a network formed from a multitude of dense layers) and compute a forward pass through the network.

The performance information 110 may therefore indicate whether the subset of devices is in a releasable state. The system 100 may use this information to inform whether the device batch 104 is releasable. In some embodiments, the system 100 may indicate that the batch of devices are releasable if all, or a threshold percentage, of the subset have positive binary values. In some embodiments, the performance information 110 may include a binary value associated with the overall batch. For example, and with respect to a neural network, an activation function in a final layer may be trained to select either a value of 0 or 1 for a batch based on the input data associated with the subset of devices.

In some embodiments, the testing data may be used during training but not during at time. As an example, the system 100 may input manufacturing data associated with a subset of devices to the machine learning model. For this example, ground truth data may be generated for the subset of devices based on the testing data. As an example, the testing data may be analyzed to determine whether a device is in a releasable condition. Thus, a binary value may be determined for each device. The machine learning model may then be trained to utilize manufacturing data for a subset of devices and output whether devices are in releasable conditions. In this way, devices may be released through application of a machine learning model without, or with more limited, time-intensive testing of the devices.

Figure 1B:
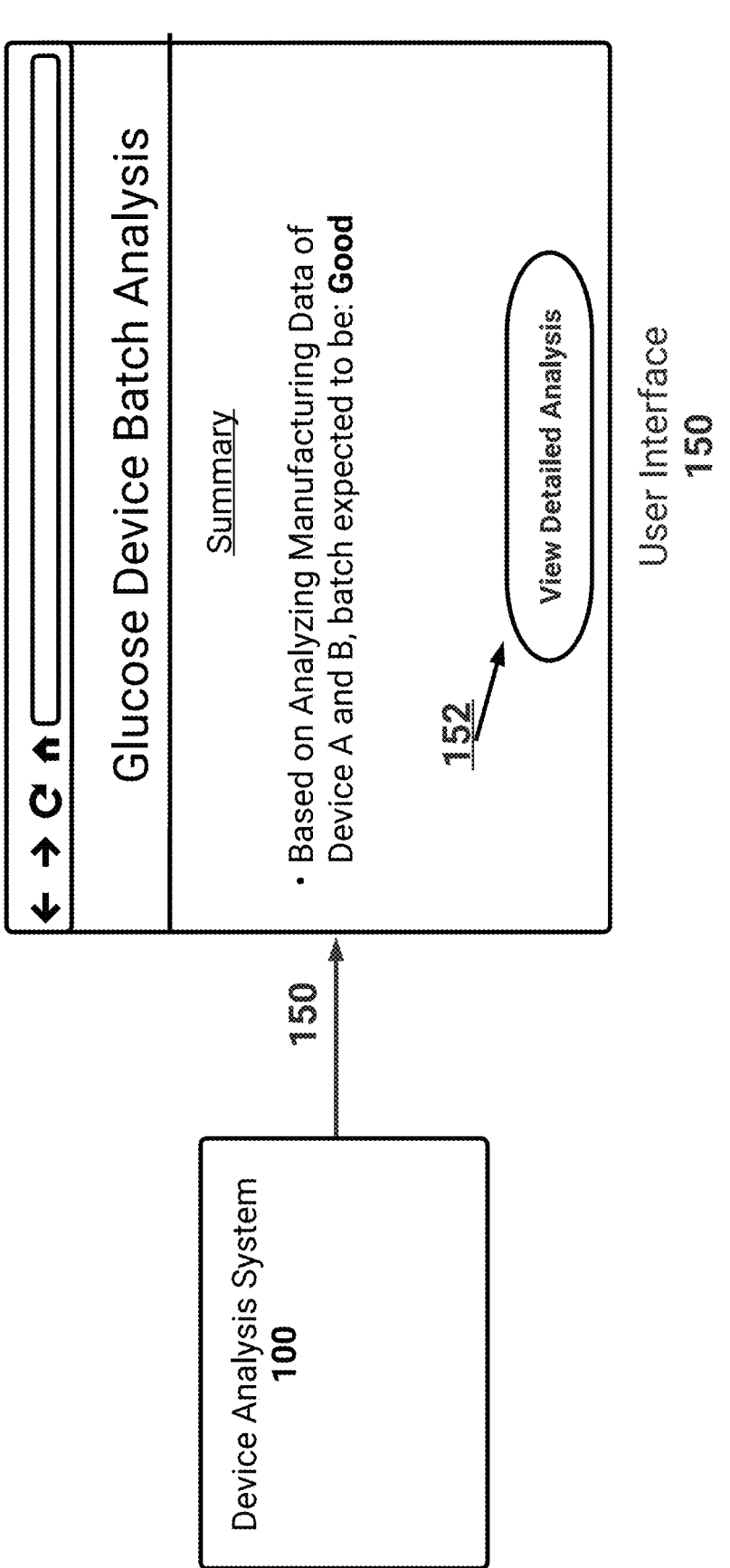
FIG. 1B is a block diagram illustrating the device analysis system presenting information via an interactive user interface.

FIG. 1B is a block diagram illustrating the device analysis system presenting information via an interactive user interface 150. The system 100 may present information describing the device batch 104 in user interface 150. For example, the system 100 may provide information for presentation in a user interface rendered by a user device (e.g., a tablet, a smart phone, a wearable device). The system 100 may also provide information for inclusion in a web application being presented via the user device. The system 100 may also render user interface 150 and the system may represent a computer used by an end-user.

In the illustrated example, user interface 150 indicates that the system 100 analyzed manufacturing data of two example devices. As described above the manufacturing data may reflect information from different portions of a manufacturing process. The user interface 150 includes a summary of the performance information determined for the devices. In this example, the summary indicates that the batch is expected to be good (e.g., in a releasable condition).

Figure 1C:
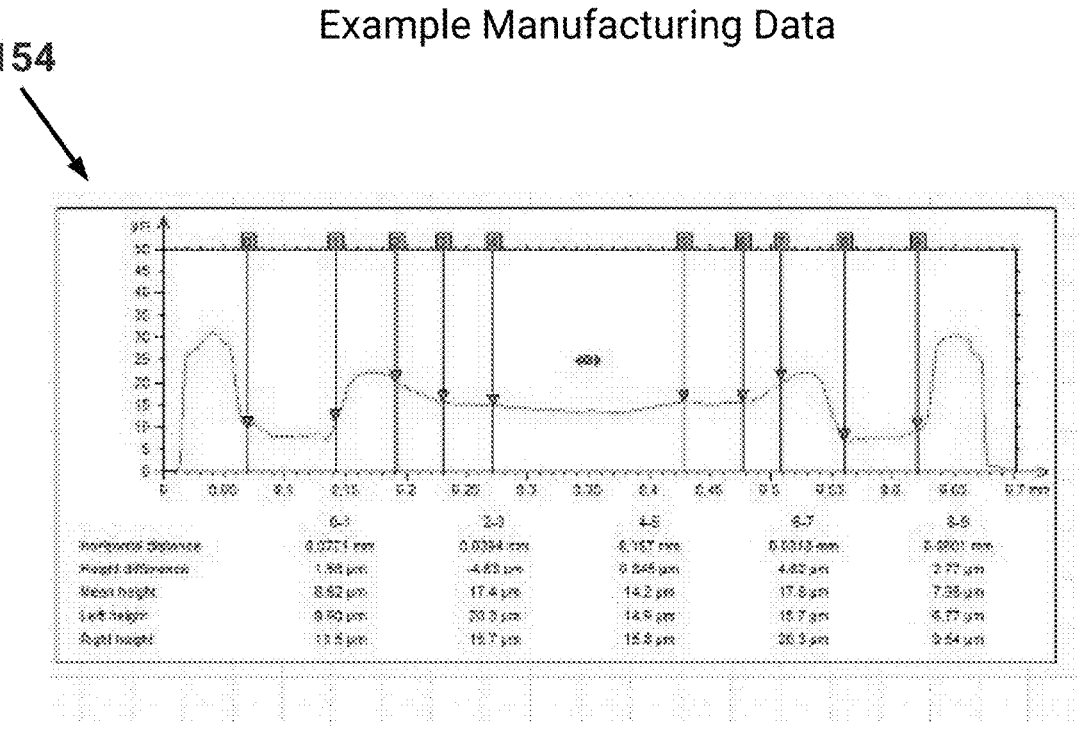
FIG. 1C illustrates graphical representations of example analysis datasets which are input into the device analysis system.

The user interface 150 additionally includes a selectable option 152 to view detailed information related to the analysis. In some embodiments, selection of the option 152 (e.g., via user input) may cause the user interface 150 to include representations of the manufacturing data. For example, FIG. 1C illustrates example manufacturing data 154. In this example, the data 154 includes a dispense profile at the top which includes measures of a glucose sensor membrane and electrolyte. The data 154 further includes manufacturing data at the bottom which indicates alignment information, placement information, leak rate (e.g., leak rate through a membrane), flow rate (e.g., flow rate through a membrane), and so on.

A user of the user interface 150 may interact with the user interface to view detailed information for a specific device and/or manufacturing stage. Additionally, the user interface 150 may indicate weighting information applied by the machine learning model to portions of the manufacturing data.

Figure 2A:
FIG. 2A illustrates detail of example analysis datasets which are input into the device analysis system.
Figure 2A:
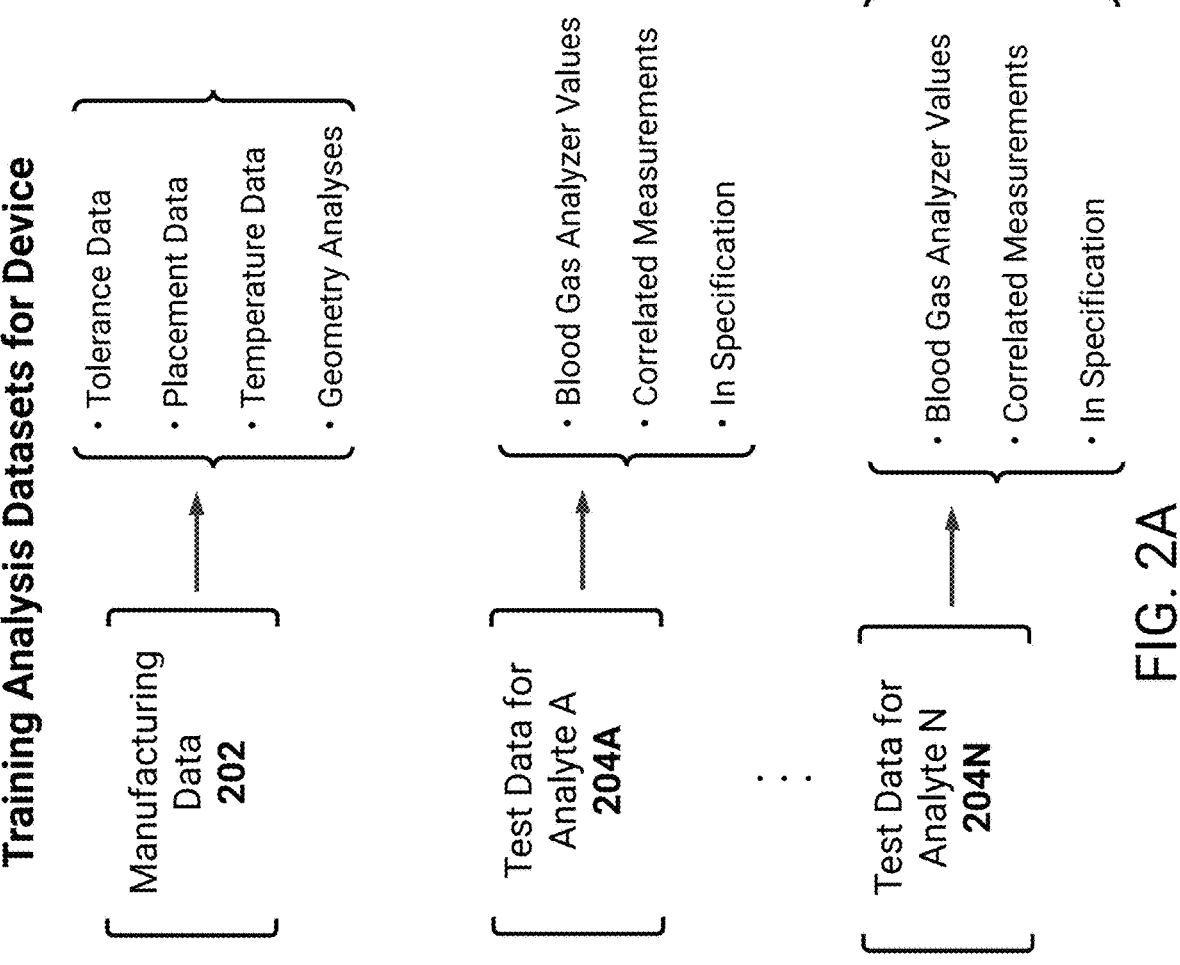

FIG. 2A illustrates detail of example analysis datasets 202-204 which are input into the device analysis system. As described above, the machine learning model described herein may be trained to output performance information based on input of manufacturing data. In some embodiments, the ground truth for the performance information may be determined based on testing of devices. Since the devices may detect different analytes, in some embodiments the training data may include test data 204A-204N for different analytes.

Example manufacturing data 202 may include some or all of the following. Additional manufacturing data 202 may be included and fall within the scope of the disclosure herein. As described above, manufacturing data 202 may be aggregated for a device based on unique identifying information (e.g., serial number). The manufacturing data 202 may represent measurements or qualities, and so on from different manufacturing stages of the devices.

For example, measurements may relate to values which indicate aspects of the devices. As another example, qualities may relate to qualitive labels which may be assigned by a system or manufacturing user. For this example, a label may be assigned by a system based on images or other sensor information of a device. An example label may indicate that a device has an occlusion (e.g., dust, particles) which are on the device. Another example label may indicate information related to a manufacturing step or process (e.g., whether the step was performed out of bounds with respect to a metric, such as time).

The manufacturing data 202 may include information related to wafer data. Example wafer data may indicate quality associated with a wafer used for a device. The data 202 may additionally include temperature calibration data. For example, the temperature calibration data may indicate how precise a manufacturing step caused a part or aspect of the device to reach a particular temperature. As another example, the temperature calibration data may reflect a variance associated with temperatures for devices included in a batch. Thus, the temperature calibration data may be specific to devices and optionally also to all devices. The manufacturing data 202 may additionally include environmental data. Example data may further include temperature or humidity information which is measured every threshold amount of time. Thus, this information may be included in logs which have substantially continuous measurements.

The manufacturing data 202 may additionally include placement data. This data may indicate how well or precise portions of a device are aligned. For example, the data may include metrics indicating offsets from ideal positions. The placement data may, in some embodiments, be automatically obtained by a system. For example, the system may image a device (e.g., when completed or at one or more of the manufacturing steps). In this example, the system may determine alignment differences for a device based on the images. As an example, the system may use a machine learning model (e.g., a convolutional neural network, attention network) to determine individual boundaries of individual parts of the device. The system may then determine the boundaries offsets from ideal placements. The system may also use a laser scanner to determine precise positions of the parts.

The manufacturing data 202 may additionally include anti-interference application data. This data may reflect an extent to which a deposited membrane is able to protect against interferents. For example, the data may indicate an extent to which the membrane stops uric acid, paracetamol, and so on.

The manufacturing data 202 may additionally include responses to solutions. For example, a voltage may be applied to the device and current coming from the device may be measured. In this example, different solutions may optionally be applied to the device while the voltage is applied.

The manufacturing data 202 may additionally include geometry data. Example data may include volumes associated with portions of a device. For example, a volume associated with a sensor membrane/electrolyte may be obtained. As another example, height information associated with a sensor membrane/electrolyte may be obtained. As another example, symmetry information associated with a portion of the device may be determined. For this example, the symmetry information may relate to the membrane of the device.

The manufacturing data 202 may additionally include production information. For example, this information may indicate a pass or fail for each stage of manufacture. As another example, this information may reflect a leak rate and/or flow rate. For this example, the leak rate and/or flow rate may relate to a rate through a membrane of a device.

The above-described manufacturing data 202 may be aggregated for individual devices. Thus, the training data may reflect the above-described data for each device which is being used for training.

Test data 204A-204N may similarly be obtained for each device which is being used for training. The test data 204A-204N a may be obtained automatically by a system or may be obtained by a manufacturing user. With respect to a system, the system may control a testing platform on which a device is placed. The testing platform may provide blood to the device and measure the device's response. The blood may be previously analyzed (e.g., via a blood gas analyzer) so that an expected response of the device may be known. The test data 204A-204N, as described above, may be specific to analytes which are able to be detected by a device.

The test data 204A-204N may include blood gas analyzer values. As described above, these values may indicate an accurate measurement associated with an analyte. Thus, these values may be used to compare against the measured responses of devices which is referred to herein as correlated measurements. The test data 204A-204N may additionally include in-specification binary values which indicate whether analytes are detected within a particular threshold range of the correlated measurements.

As will be described in FIG. 2B, the manufacturing data 202 may be used as input data to the machine learning model. Similarly, the test data 204A-204N may be used as ground truth for the output. Specifically, the test data 204A-204N may be analyzed to transform it into discrete output which the machine learning model is expected to learn. For example, the output may reflect binary values indicating whether devices are in releasable condition.

Figure 2B:
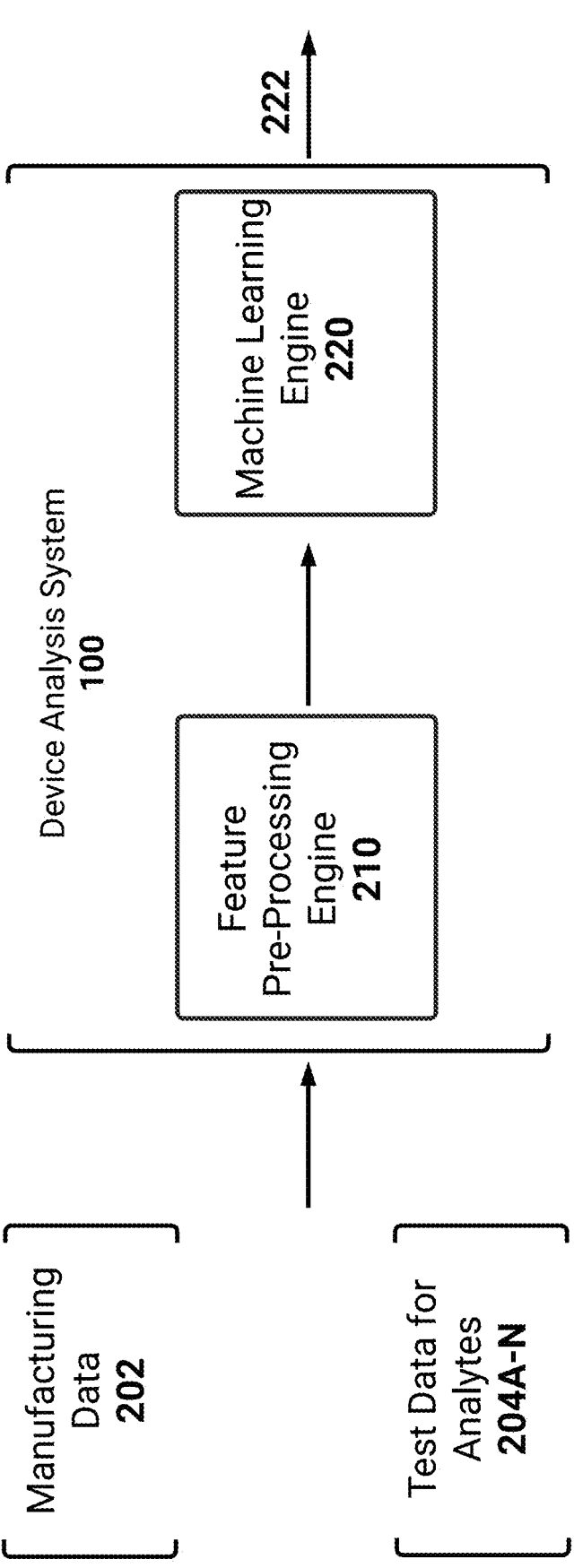
FIG. 2B illustrates detail of the device analysis system determining performance information based on the example analysis datasets.

FIG. 2B illustrates detail of the device analysis system 100 determining performance information 222 based on the example analysis datasets 202-204N. The manufacturing data 202, as described above, may be used as input to a machine learning engine 220. The test data 204A-204N may be used to generate ground truth, or expected output, from the machine learning engine 220. The engine 220 may implement one or more machine learning models which are trained to output performance information. Training may be performed using techniques known in the art, for example back-propagation.

The device analysis system 100 includes a feature pre-processing engine 210 which converts the data 202-204N into formats usable to train the machine learning model. As an example, the engine 210 may form data structure (e.g., vectors) for individual devices which aggregate manufacturing data for the individual devices.

As another example, the feature pre-processing engine 210 may adjust the test data 204A-204N into ground truth which is used to train the machine learning model. For example, and with respect to an example analyte, the engine 210 may determine whether a device has acceptable performance (e.g., in a releasable condition) based on analyzing the test data. In this example, the engine 210 may assign a binary value to each device indicating whether the device has acceptable performance. Optionally, the engine 210 may assign a score which is indicative of a performance metric with the score optionally being within a range (e.g., between zero and one).

The feature pre-processing engine 210 may access, for each device, test data related to individual analytes. As described above, the test data may reflect an expected response to an analyte (referred to herein as a blood gas analyzer (BGA) measurement). For example, blood with a known quantity of an analyte may be obtained. The test data may additionally reflect an actual response to the analyte (referred to herein as a correlated measurement). For example, the blood may be deposited onto each device and the response measured. The test data may additionally reflect an in-specification binary value which indicates whether, for an analyte, whether a device is in-specification. The in-specification value may indicate that the difference between the correlated measurement and BGA measurement is within a particular specification.

As an example, for a device with unique identifying information the pre-processing engine 210 may generate information a portion of which is reflected in the following Table 1. For each analyte, there may be a threshold number of correlated measurements (e.g., 1, 10, 25, 50, and so on).

| Serial No. | BGA Measurements | Correlated Measurements | In-specification |
|---|---|---|---|
| Unique dev ID | Numerical Val | Numerical Val | Binary |
| | Numerical Val | Numerical Val | Binary |

The pre-processing engine 210 may, in some embodiments, reduce the above via combining the BGA and correlated measurements into a single value. For example, an absolute difference may be obtained:

$$\text{Absolute Difference} = \frac{|BGA \text{ Measurement} - \text{Correlated Measurement}|}{BGA \text{ Measurement}} * 100$$

The pre-processing engine 210 may additionally compute a measure of central tendency of the absolute differences for a device. For example, an average may be obtained by summing the absolute differences and dividing by the number of measurements. In this example, a single absolute difference value may be assigned for an individual analyte or for all analytes.

The in-specification binary value may be identified based on the absolute difference value described above. For example, a positive value may be set for an analyte based on the measure of central tendency of absolute differences for that analyte being greater than a threshold (e.g., 65%, 70%, 80%, and so on).

The pre-processing engine 210 may then generate a target vector which is used as ground truth. The target vector may include performance information identifying, for example, a binary value as to whether a device has acceptable performance (e.g., is in a releasable condition). The target vector may be determined based on the in-specification values determined for the analytes.

For example, Table 2 below illustrates use of 7 analytes and in-specification values determined for each analyte.

TABLE 2

| Device ID | Glu | CO2 | O2 | Na | K | pH | HCT | Device Score | Target Vector |
|---|---|---|---|---|---|---|---|---|---|
| Dev 1 | 1 | 1 | 1 | 1 | 1 | 1 | 1 | 7 | 0 |
| Dev 2 | 0 | 1 | 0 | 0 | 1 | 1 | 1 | 4 | 1 |

In the above table, a target vector is assigned a binary value based on a device score. The device score may be a sum of the in-specification values for each device. In some embodiments, the target vector may be set to positive if the device score is greater than a threshold value or percentage (e.g., for 7 analytes, a device score 5, 6, and so on, may be required).

Thus, the pre-processing engine 210 may determine, for each device, whether the device has acceptable performance. While Table 2 identifies use of a binary value for a target vector, as described above in some embodiments a value may be selected within a range that indicates a performance score or value.

The device analysis system 100 further includes a machine learning engine 220 which causes training, and inference, of one or more machine learning models. An example machine learning model may include a clustering model (e.g., k-means clustering). Another example machine learning model may include a support vector machine. Another example machine learning model may include a neural network. In some embodiments, a combination of machine learning models may be used. For example, a first machine learning model (e.g., a neural network) may receive manufacturing data and output respective information (e.g., scores, vectors) for each manufacturing step or process. In this example, a second machine learning model (e.g., a classifier) may determine performance information (e.g., a binary value) based on the output of the neural network.

The machine learning engine 220 may train the machine learning model(s) based on the manufacturing data 202 and ground truth (e.g., the target vector). Without being constrained by way of example, as may be appreciated there are a number of training techniques for machine learning models. For example, back propagation techniques may be used. As another example, and with respect to a support vector machine, different kernels may be used. Once trained, the machine learning engine 220 may determine performance information based on input of manufacturing data.

Example Flowchart

Figure 3:
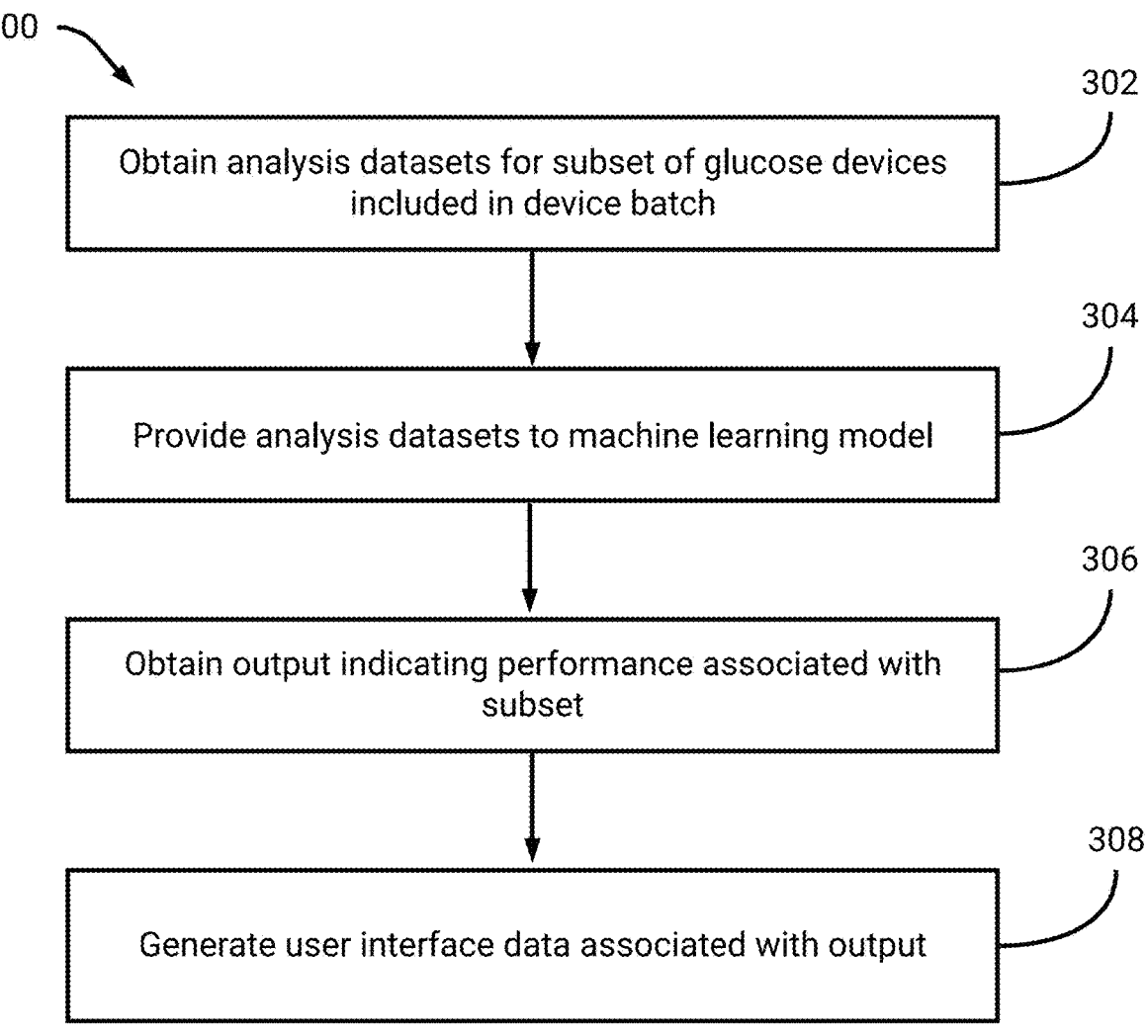
FIG. 3 is a flowchart of an example process for output performance information associated with a device batch.

FIG. 3 is a flowchart of an example process 300 for outputting performance information associated with a device batch. For convenience, the process 300 will be described as being performed by a system of one or more processors (e.g., the device analysis system 100).

At block 302, the system obtains analysis datasets for a subset of devices included in a device batch. As described above, the devices may be medical devices (e.g., glucose devices) which were manufactured. The analysis datasets may reflect the above-described manufacturing data and may be specific to individual devices in the subset. In some embodiments, manufacturing data for all the devices in the device batch may be used.

At block 304, the system provides the analysis datasets as input to a machine learning model. For example, and with respect to a neural network, the system computes a forward pass.

At block 306, the system obtains output indicating performance information associated with the subset. As described above, in some embodiments the performance information may indicate a binary value for each device which identifies whether the device is in a releasable condition.

At block 308, the system generates user interface data associated with the output. The user interface describes whether the batch is expected to be in a releasable condition, with an example included in FIG. 1B. The user interface may additionally indicate whether any manufacturing steps or processes were missed. For example, the system may analyze the manufacturing data to ensure that manufacturing data from all manufacturing steps or processes was included.

In some embodiments, the user interface may identify whether a manufacturing step or process was unusually performed. For example, the system may determine average values for a particular manufacturing step. In this example, the system may determine that for the batch the manufacturing step was performed out of bounds due to values being greater than a threshold different from the averages. In some embodiments, the system may cause presentation of images or video depicting the devices undergoing to the manufacturing step or process.

OTHER EMBODIMENTS

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure.

For example, the functionality described herein may be performed as software instructions are executed by, and/or in response to software instructions being executed by, one or more hardware processors and/or any other suitable computing devices. The software instructions and/or other executable code may be read from a computer readable storage medium (or mediums).

The computer readable storage medium can be a tangible device that can retain and store data and/or instructions for use by an instruction execution device. The computer readable storage medium may be, for example, but is not limited to, an electronic storage device (including any volatile and/or non-volatile electronic storage devices), a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a solid state drive, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions (as also referred to herein as, for example, "code," "instructions," "module," "application," "software application," and/or the like) for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Java, C++, or the like, and procedural programming languages, such as the "C" programming language or similar programming languages. Computer readable program instructions may be callable from other instructions or from itself, and/or may be invoked in response to detected events or interrupts. Computer readable program instructions configured for execution on computing devices may be provided on a computer readable storage medium, and/or as a digital download (and may be originally stored in a compressed or installable format that requires installation, decompression or decryption prior to execution) that may then be stored on a computer readable storage medium. Such computer readable program instructions may be stored, partially or fully, on a memory device (e.g., a computer readable storage medium) of the executing computing device, for execution by the computing device. The computer readable program instructions may execute entirely on a user's computer (e.g., the executing computing device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. For example, the instructions may initially be carried on a magnetic disk or solid state drive of a remote computer. The remote computer may load the instructions and/or modules into its dynamic memory and send the instructions over a telephone, cable, or optical line using a modem. A modem local to a server computing system may receive the data on the telephone/cable/optical line and use a converter device including the appropriate circuitry to place the data on a bus. The bus may carry the data to a memory, from which a processor may retrieve and execute the instructions. The instructions received by the memory may optionally be stored on a storage device (e.g., a solid state drive) either before or after execution by the computer processor.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. In addition, certain blocks may be omitted in some implementations. The methods and processes described herein are also not limited to any particular sequence, and the blocks or states relating thereto can be performed in other sequences that are appropriate.

It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions. For example, any of the processes, methods, algorithms, elements, blocks, applications, or other functionality (or portions of functionality) described in the preceding sections may be embodied in, and/or fully or partially automated via, electronic hardware such application-specific processors (e.g., application-specific integrated circuits (ASICs)), programmable processors (e.g., field programmable gate arrays (FPGAs)), application-specific circuitry, and/or the like (any of which may also combine custom hard-wired logic, logic circuits, ASICs, FPGAs, etc. with custom programming/execution of software instructions to accomplish the techniques).

Any of the above-mentioned processors, and/or devices incorporating any of the above-mentioned processors, may be referred to herein as, for example, "computers," "computer devices," "computing devices," "hardware computing devices," "hardware processors," "processing units," and/or the like. Computing devices of the above-embodiments may generally (but not necessarily) be controlled and/or coordinated by operating system software, such as Mac OS, iOS, Android, Chrome OS, Windows OS (e.g., Windows XP, Windows Vista, Windows 7, Windows 8, Windows 10, Windows Server, etc.), Windows CE, Unix, Linux, SunOS, Solaris, Blackberry OS, VxWorks, or other suitable operating systems. In other embodiments, the computing devices may be controlled by a proprietary operating system. Conventional operating systems control and schedule computer processes for execution, perform memory management, provide file system, networking, I/O services, and provide a user interface functionality, such as a graphical user interface ("GUI"), among other things.

Figure 4:
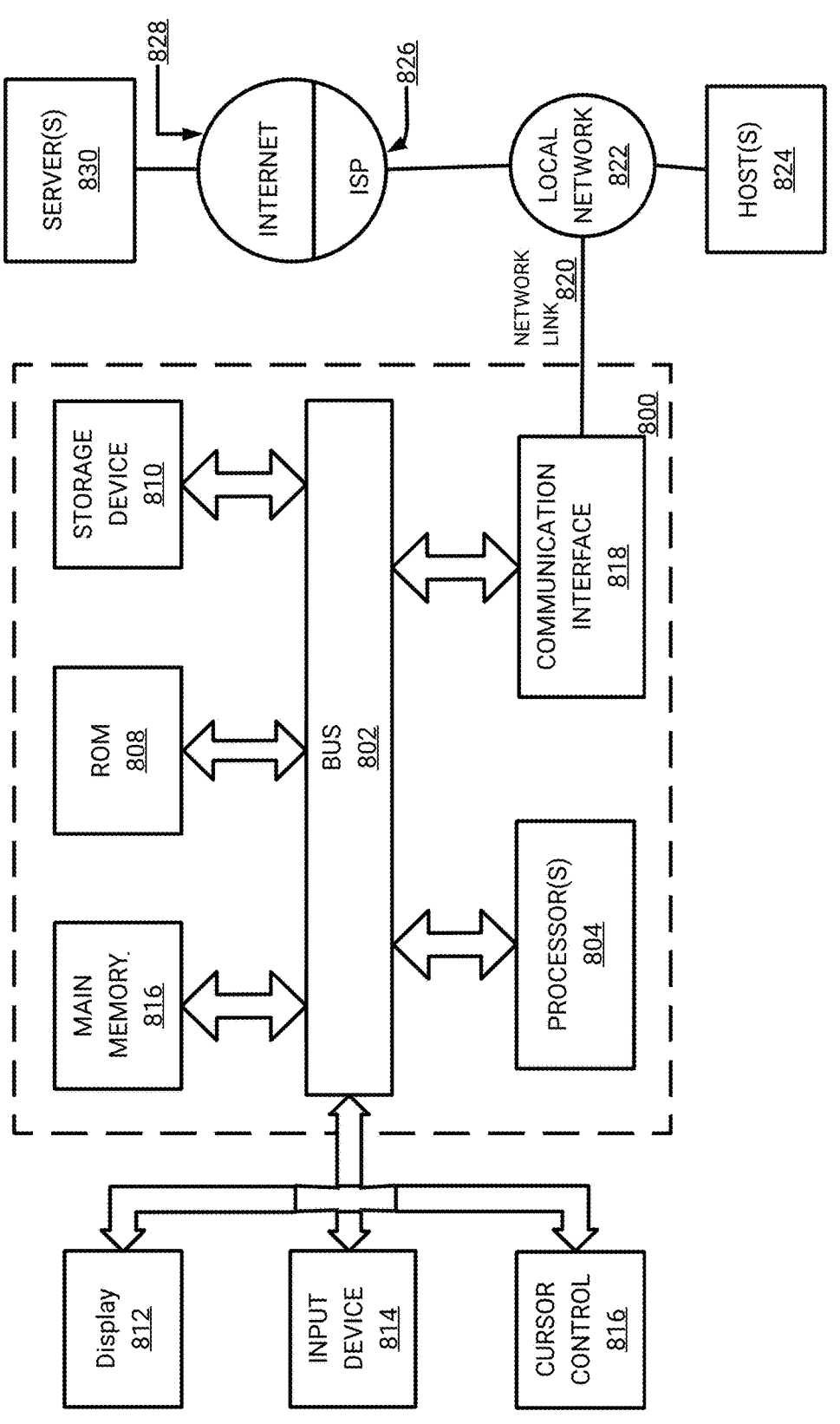
FIG. 4 illustrates an embodiment of a computing device according to the present disclosure.

For example, FIG. 4 is a block diagram that illustrates a computer system 400 upon which various embodiments may be implemented. Computer system 400 includes a bus 402 or other communication mechanism for communicating information, and a hardware processor, or multiple processors, 404 coupled with bus 402 for processing information. Hardware processor(s) 404 may be, for example, one or more general purpose microprocessors.

Computer system 400 also includes a main memory 406, such as a random access memory (RAM), cache and/or other dynamic storage devices, coupled to bus 402 for storing information and instructions to be executed by processor 404. Main memory 406 also may be used for storing temporary variables or other intermediate information during execution of instructions to be executed by processor 404. Such instructions, when stored in storage media accessible to processor 404, render computer system 400 into a special-purpose machine that is customized to perform the operations specified in the instructions.

Computer system 400 further includes a read only memory (ROM) 408 or other static storage device coupled to bus 402 for storing static information and instructions for processor 404. A storage device 410, such as a magnetic disk, optical disk, or USB thumb drive (Flash drive), etc., is provided and coupled to bus 402 for storing information and instructions.

Computer system 400 may be coupled via bus 402 to a display 412, such as a cathode ray tube (CRT) or LCD display (or touch screen), for displaying information to a computer user. An input device 414, including alphanumeric and other keys, is coupled to bus 402 for communicating information and command selections to processor 404. Another type of user input device is cursor control 416, such as a mouse, a trackball, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen without a cursor.

Computing system 400 may include a user interface module to implement a GUI that may be stored in a mass storage device as computer executable program instructions that are executed by the computing device(s). Computer system 400 may further, as described below, implement the techniques described herein using customized hard-wired logic, one or more ASICs or FPGAs, firmware and/or program logic which in combination with the computer system causes or programs computer system 400 to be a special-purpose machine. According to one embodiment, the techniques herein are performed by computer system 400 in response to processor(s) 404 executing one or more sequences of one or more computer readable program instructions contained in main memory 406. Such instructions may be read into main memory 406 from another storage medium, such as storage device 410. Execution of the sequences of instructions contained in main memory 406 causes processor(s) 404 to perform the process steps described herein. In alternative embodiments, hard-wired circuitry may be used in place of or in combination with software instructions.

Various forms of computer readable storage media may be involved in carrying one or more sequences of one or more computer readable program instructions to processor 404 for execution. For example, the instructions may initially be carried on a magnetic disk or solid state drive of a remote computer. The remote computer can load the instructions into its dynamic memory and send the instructions over a telephone line using a modem. A modem local to computer system 400 can receive the data on the telephone line and use an infra-red transmitter to convert the data to an infra-red signal. An infra-red detector can receive the data carried in the infra-red signal and appropriate circuitry can place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated services digital network (ISDN) card, cable modem, satellite modem, or a modem to provide a data communication connection to a corresponding type of telephone line. As another example, communication interface 418 may be a local area network (LAN) card to provide a data communication connection to a compatible LAN (or WAN component to communicated with a WAN). Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the world wide packet data communication network now commonly referred to as the "Internet" 428. Local network 422 and Internet 428 both use electrical, electromagnetic or optical signals that carry digital data streams. The signals through the various networks and the signals on network link 420 and through communication interface 418, which carry the digital data to and from computer system 400, are example forms of transmission media.

Computer system 400 can send messages and receive data, including program code, through the network(s), network link 420 and communication interface 418. In the Internet example, a server 430 might transmit a requested code for an application program through Internet 428, ISP 426, local network 422 and communication interface 418.

The received code may be executed by processor 404 as it is received, and/or stored in storage device 410, or other non-volatile storage for later execution.

As described above, in various embodiments certain functionality may be accessible by a user through a user interface (e.g., an interactive user interface, for example via a web-based viewer such as a web browser, or other suitable software program). In such implementations, the user interface may be generated by a server computing system and transmitted to a web browser of the user (e.g., running on the user's computing system). Alternatively, data (e.g., user interface data) necessary for generating the user interface may be provided by the server computing system to the browser, where the user interface may be generated (e.g., the user interface data may be executed by a browser accessing a web service and may be configured to render the user interfaces based on the user interface data). The user may then interact with the user interface through the web-browser. User interfaces of certain implementations may be accessible through one or more dedicated software applications. In certain embodiments, one or more of the computing devices and/or systems of the disclosure may include mobile computing devices, and user interfaces may be accessible through such mobile computing devices (for example, smartphones and/or tablets).

Many variations and modifications may be made to the above-described embodiments, the elements of which are to be understood as being among other acceptable examples. All such modifications and variations are intended to be included herein within the scope of this disclosure. The foregoing description details certain embodiments. It will be appreciated, however, that no matter how detailed the foregoing appears in text, the systems and methods can be practiced in many ways. As is also stated above, it should be noted that the use of particular terminology when describing certain features or aspects of the systems and methods should not be taken to imply that the terminology is being re-defined herein to be restricted to including any specific characteristics of the features or aspects of the systems and methods with which that terminology is associated.

Conditional language, such as, among others, "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

The term "substantially" when used in conjunction with the term "real-time" forms a phrase that will be readily understood by a person of ordinary skill in the art. For example, it is readily understood that such language will include speeds in which no or little delay or waiting is discernible, or where such delay is sufficiently short so as not to be disruptive, irritating, or otherwise vexing to a user.

Conjunctive language such as the phrase "at least one of X, Y, and Z," or "at least one of X, Y, or Z," unless specifically stated otherwise, is to be understood with the context as used in general to convey that an item, term, etc. may be either X, Y, or Z, or a combination thereof. For example, the term "or" is used in its inclusive sense (and not in its exclusive sense) so that when used, for example, to connect a list of elements, the term "or" means one, some, or all of the elements in the list. Thus, such conjunctive language is not generally intended to imply that certain embodiments require at least one of X, at least one of Y, and at least one of Z to each be present.

The term "a" as used herein should be given an inclusive rather than exclusive interpretation. For example, unless specifically noted, the term "a" should not be understood to mean "exactly one" or "one and only one"; instead, the term "a" means "one or more" or "at least one," whether used in the claims or elsewhere in the specification and regardless of uses of quantifiers such as "at least one," "one or more," or "a plurality" elsewhere in the claims or specification.

The term "comprising" as used herein should be given an inclusive rather than exclusive interpretation. For example, a general purpose computer comprising one or more processors should not be interpreted as excluding other computer components, and may possibly include such components as memory, input/output devices, and/or network interfaces, among others.

While the above detailed description has shown, described, and pointed out novel features as applied to various embodiments, it may be understood that various omissions, substitutions, and changes in the form and details of the devices or processes illustrated may be made without departing from the spirit of the disclosure. As may be recognized, certain embodiments of the inventions described herein may be embodied within a form that does not provide all of the features and benefits set forth herein, as some features may be used or practiced separately from others. The scope of certain inventions disclosed herein is indicated by the appended claims rather than by the foregoing description. All changes which come within the meaning and range of equivalency of the claims are to be embraced within their scope.

OTHER EMBODIMENTS

All of the processes described herein may be embodied in, and fully automated, via software code modules executed by a computing system that includes one or more computers or processors. The code modules may be stored in any type of non-transitory computer-readable medium or other computer storage device. Some or all the methods may be embodied in specialized computer hardware.

Many other variations than those described herein will be apparent from this disclosure. For example, depending on the embodiment, certain acts, events, or functions of any of the algorithms described herein can be performed in a different sequence or can be added, merged, or left out altogether (for example, not all described acts or events are necessary for the practice of the algorithms). Moreover, in certain embodiments, acts or events can be performed concurrently, for example, through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and engines described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, for example, a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

Conditional language such as, among others, "can," "could," "might" or "may," unless specifically stated otherwise, are understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," unless specifically stated otherwise, is understood with the context as used in general to present that an item, term, etc., may be either X, Y, or Z, or any combination thereof (for example, X, Y, and/or Z). Thus, such disjunctive language is not generally intended to, and should not, imply that certain embodiments require at least one of X, at least one of Y, or at least one of Z to each be present.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

It should be emphasized that many variations and modifications may be made to the above-described embodiments, the elements of which are to be understood as being among other acceptable examples. All such modifications and variations are intended to be included herein within the scope of this disclosure.

What is claimed is:

1. A method implemented by a system of one or more processors, the method comprising:

obtaining analysis datasets reflecting manufacturing information associated with a plurality of medical devices included in a device batch, the manufacturing data measuring information associated with individual manufacturing steps of a plurality of manufacturing steps, wherein at least a subset of the analysis datasets are automatically obtained from systems which associated with individual manufacturing stages, and wherein obtaining an individual dataset comprises:

accessing sensor data associated with, at least, visual characteristics of the medical devices, the sensor data being derived from one or more sensors, and generating placement data indicative of alignment of the medical devices during manufacture, the placement data being generated via analyzing the sensor data and indicating, at least, a metric associated with a distinction in placement of an individual medical device from a desired placement;

formatting the analysis datasets for input into a machine learning model, and aggregating analysis datasets specific to the medical devices based on unique identifying information associated with the medical devices;

determining output via the machine learning model based on the analysis datasets, wherein a forward pass is computed through the machine learning model and wherein the output includes performance information for individual medical devices of the plurality of medical devices, wherein the machine learning model was trained based on ground truth associated with manufactured devices, the ground truth being derived based on test information associated with the manufactured devices, and wherein the performance information is indicative of the devices being in releasable condition; and generating an interactive user interface which presents summary information associated with the performance information.

2. The method of claim 1, wherein the devices are glucose devices and wherein the manufacturing data reflects information indicating accurate placement of a membrane configured to detect glucose.

3. The method of claim 1, wherein the devices are configured to detect a plurality of analytes, and wherein the manufacturing data is specific to individual analytes.

4. The method of claim 1, wherein generating the test information comprises:

determining, for each manufactured device, measures of difference between expected responses to individual analytes of a plurality of analytes and actual responses of the devices; and generating, based on the measures, a target vector indicating whether the manufactured devices have performance greater than a threshold, wherein the target vector includes a binary value for each manufactured device.

5. The method of claim 4, wherein generating the target vector comprises:

assigning, for each analyte of individual manufactured devices, a binary value indicating whether the individual manufactured devices are in specification; and determining, based on the binary values, whether each manufactured device has performance greater than a threshold.

6. The method of claim 1, wherein the interactive user interface responds to user input associated with requesting detailed information, and wherein the interactive user interface updates to reflect graphical representations of the manufacturing information.

7. The method of claim 1, wherein the interactive user interface indicates a manufacturing step which was not performed, or which was performed out of bounds as compared to normal performance.

8. Non-transitory computer storage media storing instructions that when executed by one or more processors, cause the one or more processors to perform operations comprising:

obtaining analysis datasets reflecting manufacturing information associated with a plurality of medical devices included in a device batch, the manufacturing data measuring information associated with individual manufacturing steps of a plurality of manufacturing steps, wherein obtaining analysis datasets comprises:

accessing sensor data associated with, at least, visual characteristics of the medical devices, the sensor data being derived from one or more sensors, and generating placement data indicative of alignment of the medical devices during manufacture, the placement data being generated via analyzing the sensor data and indicating, at least, a metric associated with a distinction in placement of an individual medical device from a desired placement;

formatting the analysis datasets for input into a machine learning model, and aggregating analysis datasets specific to the medical devices based on unique identifying information associated with the medical devices;

determining output via the machine learning model based on the analysis datasets, wherein the output includes performance information for individual medical devices of the plurality of medical devices, wherein the machine learning model was trained based on ground truth associated with manufactured devices, the ground truth being derived based on test information associated with the manufactured devices, and wherein the performance information is indicative of the devices being in releasable condition; and generating an interactive user interface which presents summary information associated with the performance information.

9. The computer storage media of claim 8, wherein the devices are glucose devices and wherein the manufacturing data reflects information indicating accurate placement of a membrane configured to detect glucose.

10. The computer storage media of claim 8, wherein the devices are configured to detect a plurality of analytes, and wherein the manufacturing data is specific to individual analytes.

11. The computer storage media of claim 8, wherein generating the test information comprises:

determining, for each manufactured device, measures of difference between expected responses to individual analytes of a plurality of analytes and actual responses of the devices; and generating, based on the measures, a target vector indicating whether the manufactured devices have performance greater than a threshold, wherein the target vector includes a binary value for each manufactured device.

12. The computer storage media of claim 11, wherein generating the target vector comprises:

assigning, for each analyte of individual manufactured devices, a binary value indicating whether the individual manufactured devices are in specification; and determining, based on the binary values, whether each manufactured device has performance greater than a threshold.

13. The computer storage media of claim 8, wherein the interactive user interface responds to user input associated with requesting detailed information, and wherein the interactive user interface updates to reflect graphical representations of the manufacturing information.

14. The computer storage media of claim 8, wherein the interactive user interface indicates a manufacturing step which was not performed, or which was performed out of bounds as compared to normal performance.

15. A system comprising one or more processors and non-transitory computer storage media storing instructions that when executed by the one or more processors, cause the processors to perform operations comprising:

obtaining analysis datasets reflecting manufacturing information associated with a plurality of medical devices included in a device batch, the manufacturing data measuring information associated with individual manufacturing steps of a plurality of manufacturing steps, wherein obtaining analysis datasets comprises:

accessing sensor data associated with, at least, visual characteristics of the medical devices, the sensor data being derived from one or more sensors, and generating placement data indicative of alignment of the medical devices during manufacture, the placement data being generated via analyzing the sensor data and indicating, at least, a metric associated with a distinction in placement of an individual medical device from a desired placement;

formatting the analysis datasets are formatted for input into a machine learning model, and aggregating analysis datasets specific to the medical devices based on unique identifying information associated with the medical devices;

determining output via providing the analysis datasets to the machine learning model based on the analysis datasets, wherein the output includes performance information for individual medical devices of the plurality of medical devices, wherein the machine learning model was trained based on ground truth associated with manufactured devices, the ground truth being derived based on test information associated with the manufactured devices, and wherein the performance information is indicative of the devices being in releasable condition; and generating an interactive user interface which presents summary information associated with the performance information.

16. The system of claim 15, wherein the devices are glucose devices and wherein the manufacturing data reflects information indicating accurate placement of a membrane configured to detect glucose.

17. The system of claim 15, wherein the devices are configured to detect a plurality of analytes, and wherein the manufacturing data is specific to individual analytes.

18. The system of claim 15, wherein generating the test information comprises:

determining, for each manufactured device, measures of difference between expected responses to individual analytes of a plurality of analytes and actual responses of the devices; and generating, based on the measures, a target vector indicating whether the manufactured devices have performance greater than a threshold, wherein the target vector includes a binary value for each manufactured device.

19. The system of claim 18, wherein generating the target vector comprises:

assigning, for each analyte of individual manufactured devices, a binary value indicating whether the individual manufactured devices are in specification; and determining, based on the binary values, whether each manufactured device has performance greater than a threshold.

20. The system of claim 15, wherein the interactive user interface responds to user input associated with requesting detailed information, and wherein the interactive user interface updates to reflect graphical representations of the manufacturing information.

* * * * *